US008168388B2

(12) United States Patent
Gormley et al.

(10) Patent No.: US 8,168,388 B2
(45) Date of Patent: May 1, 2012

(54) PREPARATION OF NUCLEIC ACID TEMPLATES FOR SOLID PHASE AMPLIFICATION

(75) Inventors: Niall Anthony Gormley, Walden (GB); Jonathan Mark Boutell, Walden (GB); Gerardo Turcatti, Walden (GB); Colin Lloyd Barnes, Walden (GB)

(73) Assignee: Illumina Cambridge Ltd, Essex (GB)

( * ) Notice: Subject to any disclaimer, the term of this patent is extended or adjusted under 35 U.S.C. 154(b) by 488 days.

(21) Appl. No.: 12/085,508

(22) PCT Filed: Nov. 24, 2006

(86) PCT No.: PCT/GB2006/004407
§ 371 (c)(1), (2), (4) Date: Oct. 26, 2009

(87) PCT Pub. No.: WO2007/060456
PCT Pub. Date: May 31, 2007

(65) Prior Publication Data
US 2010/0041561 A1    Feb. 18, 2010

(30) Foreign Application Priority Data
Nov. 25, 2005  (GB) .................................. 0524069.2

(51) Int. Cl.
*C12Q 1/68* (2006.01)
*C12P 19/34* (2006.01)
(52) U.S. Cl. ...................... 435/6.12; 435/91.1; 435/91.2
(58) Field of Classification Search ................. 435/91.1, 435/91.2, 6.12
See application file for complete search history.

(56) References Cited

U.S. PATENT DOCUMENTS

| | | | |
|---|---|---|---|
| 4,719,179 A | 1/1988 | Barany | |
| 5,093,245 A | 3/1992 | Keith et al. | |
| 5,326,692 A | 7/1994 | Brinkley et al. | |
| 5,436,142 A | 7/1995 | Wigler et al. | |
| 5,508,169 A | 4/1996 | Deugau et al. | |
| 5,514,539 A | 5/1996 | Bukh et al. | |
| 5,589,332 A | 12/1996 | Shih et al. | |
| 5,616,478 A | 4/1997 | Chetverin et al. | |
| 5,641,658 A | 6/1997 | Adams et al. | |

(Continued)

FOREIGN PATENT DOCUMENTS
EP  0 201 184   12/1986
(Continued)

OTHER PUBLICATIONS

Adessi et al., Solid phase DNA amplification: characterisation of primer attachment and amplification mechanisms, Nucleic Acids Research, 28:e87; 1-8 (2000).

(Continued)

*Primary Examiner* — Kenneth R. Horlick
(74) *Attorney, Agent, or Firm* — Tiffany B. Thomas

(57) ABSTRACT

The invention relates to a method of preparing template constructs for solid-phase nucleic acid amplification and to use of the templates in methods of solid-phase nucleic acid amplification. The method involves carrying out two ligation reactions: (a) a ligation reaction in which the first end of one or more target polynucleotide molecules are ligated to surface-bound adaptor polynucleotide molecules, and (b) a ligation reaction in which solution-phase adaptor polynucleotide molecules are ligated to the second end of said target polynucleotide molecules, in order to produce one or more template constructs attached to a solid support.

32 Claims, 3 Drawing Sheets

U.S. PATENT DOCUMENTS

| | | | |
|---|---|---|---|
| 5,645,994 A | 7/1997 | Huang | |
| 5,750,337 A | 5/1998 | Squirrell | |
| 5,753,439 A | 5/1998 | Smith et al. | |
| 5,759,822 A | 6/1998 | Chenchik et al. | |
| 5,800,992 A | 9/1998 | Fodor et al. | |
| 5,837,466 A | 11/1998 | Lane et al. | |
| 5,843,660 A | 12/1998 | Schumm et al. | |
| 5,939,291 A | 8/1999 | Loewy et al. | |
| 5,942,391 A | 8/1999 | Zhang et al. | |
| 6,033,881 A | 3/2000 | Himmler et al. | |
| 6,045,994 A | 4/2000 | Zabeau et al. | |
| 6,054,276 A | 4/2000 | Macevicz | |
| 6,060,288 A | 5/2000 | Adams et al. | |
| 6,090,592 A | 7/2000 | Adams et al. | |
| 6,107,023 A | 8/2000 | Reyes et al. | |
| 6,114,149 A | 9/2000 | Fry et al. | |
| 6,261,770 B1 | 7/2001 | Warthoe | |
| 6,261,782 B1 * | 7/2001 | Lizardi et al. | 435/6.12 |
| 6,277,606 B1 | 8/2001 | Wigler et al. | |
| 6,287,825 B1 | 9/2001 | Weissman et al. | |
| 6,361,947 B1 | 3/2002 | Dong et al. | |
| 6,372,434 B1 | 4/2002 | Weissman et al. | |
| 6,383,754 B1 * | 5/2002 | Kaufman et al. | 435/6.12 |
| 6,395,887 B1 | 5/2002 | Weissman et al. | |
| 6,406,893 B1 | 6/2002 | Knapp et al. | |
| 7,115,400 B1 | 10/2006 | Adessi et al. | |
| 7,741,463 B2 * | 6/2010 | Gormley et al. | 536/23.1 |
| 2004/0067493 A1 | 4/2004 | Matsuzaki et al. | |
| 2004/0137473 A1 | 7/2004 | Wigler et al. | |
| 2004/0209299 A1 * | 10/2004 | Pinter et al. | 435/6 |
| 2005/0095645 A1 | 5/2005 | Jones et al. | |
| 2005/0100900 A1 | 5/2005 | Kawashima et al. | |
| 2007/0128624 A1 | 6/2007 | Gormley et al. | |

FOREIGN PATENT DOCUMENTS

| | | |
|---|---|---|
| EP | 0 224 126 | 6/1987 |
| EP | 0 356 025 | 4/1994 |
| EP | 0 665 293 | 8/1995 |
| EP | 0 543 484 | 1/2001 |
| GB | 2 412 170 | 9/2005 |
| WO | WO 87/06270 | 10/1987 |
| WO | WO 89/12695 | 12/1989 |
| WO | WO 91/06678 | 5/1991 |
| WO | WO 93/04199 | 3/1993 |
| WO | WO 94/02634 | 2/1994 |
| WO | WO 94/03624 | 2/1994 |
| WO | WO 95/33073 | 12/1995 |
| WO | WO 96/04404 | 2/1996 |
| WO | WO 96/32504 | 10/1996 |
| WO | WO 97/04126 | 2/1997 |
| WO | WO 97/46704 | 12/1997 |
| WO | WO 97/47767 | 12/1997 |
| WO | WO 98/15652 | 4/1998 |
| WO | WO 98/36094 | 8/1998 |
| WO | WO 98/44151 | 10/1998 |
| WO | WO 98/44152 | 10/1998 |
| WO | WO 98/45474 | 10/1998 |
| WO | WO 00/18957 | 4/2000 |
| WO | WO 00/23620 | 4/2000 |
| WO | WO 00/41524 | 7/2000 |
| WO | WO 00/47767 | 8/2000 |
| WO | WO 01/61036 | 8/2001 |
| WO | WO 03/012118 | 2/2003 |
| WO | WO 2004/070007 | 8/2004 |
| WO | WO 2004/081183 | 9/2004 |
| WO | WO 2005/068656 | 7/2005 |
| WO | WO 2005/090599 | 9/2005 |
| WO | WO 2007/010251 | 1/2007 |

OTHER PUBLICATIONS

Chang et al., PCR Amplification of Chromosome-Specific DNA Isolated from Flow Cytometry-Sorted Chromosomes, Genomics, 12:307-312 (1992).

Chenchik et al., Full-Length cDNA Cloning and Determination of mRNA 5' and 3' Ends by Amplification of Adaptor-Ligated cDNA, BioTechniques, 21:526-534 (1996).

Cheng et al., Chip PCR. II. Investigation of different PCR amplification systems in microfabricated silicon-glass chips, Nucleic Acids Research, 24:380-385 (1996).

Dubiley et al., Polymorphism analysis and gene detection by minisequencing on an array of gel-immobilized primers, Nucleic Acids Research, 27:e19; i-vi (1999).

Ferguson et al., A fiber-optic DNA biosensor microarray for the analysis of gene expression, Nature Biotechnology 14:1681-1684 (1996).

Fu et al., Sequencing double-stranded DNA by strand displacement, Nucleic Acids Research, 25:677-679 (1997).

Gubler et al., A simple and very efficient method for generating cDNA libraries, Gene, 25:263-269 (1983).

Hahn et al., Quantitative polymerase chain reaction with enzyme-linked immunosorbent assay detection of selectively digested amplified sample and control DNA, Anal, Biochem, 229:236-248 (1995).

Helfman et al., Identification of clones that encode chicken tropomyosin by direct immunological screening of a cDNA expression library, Proc. Natl. Acad. Sci, 80:31-35 (1983).

Johnson, Molecular Cloning of DNA from Specific Chromosomal Regions by Microdissection and Sequence-Independent Amplification of DNA, Genomics, 6:243-251 (1990).

Kalisch et al., Covalently linked sequencing primer linkers (splinkers) for sequence analysis of restriction fragments, Gene, 44:263-270 (1986).

Kimmel et al., Preparation of cDNA and the Generation of cDNA Libraries: Overview, in Methods in Enzymology, 152:307-316 (1987).

Kinzler et al., Whole genome PCR: application to the identification of sequences bound by gene regulatory proteins, Nucleic Acids Research, 17:3645-3653 (1989).

Lizardi et al., Mutation detection and single-molecule counting using isothermal rolling-circle amplification, Nature Genetics,19:225-232 (1998).

Lockhart et al., Expression monitoring by hybridization to high-density oligonucleotide arrays, Nature Biotechnology, 14:1675-1680 (1996).

Lucito et al., Genetic analysis using genomic representations, Proc. Natl. Acad. Sci USA, 95:4487-4492 (1998).

Matsunaga et al., Selecting and amplifying one fragment from DNA fragment mixture by polymerase chain reaction with a pair of selective primers, Electrophoresis, 17:1833-1840 (1996).

Mitra et al., In situ localized amplification and contact replication of many individual DNA molecules, Nucleic Acid Research, 27:e34, i-vi; (1999).

Matsuzaki et al., Parallel Genotyping of Over 10,000 SNPs Using a One-Primer Assay on a High-Density Oligonucleotide Array, Genome Research, 14:414-425 (2004).

Mueller et al., in Vivo Footprinting of a Muscle Specific Enhancer by Ligation Mediated PCR, Science, 246:780-786 (1989).

Notomi et al., Loop-mediated isothermal amplification of DNA, Nucleic Acids Research, 28:e63; i-vii (2000).

Nussbaum et al., Isolation of anonymous DNA sequences from within a submicroscopic X chromosomal deletion in a patient with choroideremia, deafness, and mental retardation, Proc. Natl. Acad. Sci. USA, 84:6521-6525 (1987).

Ochman et al., Genetic Applications of an Inverse Polymerase Chain Reaction, Genetics, 120:621-623 (1988).

Oliphant et al., Cloning of random-sequence oligodeoxynucleotides, Gene, 44:177-183 (1986).

Oroskar et al., Detection of immobilized amplicons by ELISA-like techniques, Clinical Chemistry, 42:1547-1555 (1996).

Pease et al., Light-generated oligonucleotide arrays for rapid DNA sequence analysis, Proc. Natl. Acad. Sci. USA, 91:5022-5026 (1994).

Pfeifer et al., Genomic Sequencing and Methylation Analysis by Ligation Mediated PCR, Science, 246:810-813 (1989).

Saiki et al., Analysis of enzymatically amplified β-globin and HLA-DQα DNA with allele-specific oligonucleotide probes, Nature, 324:163-166 (1986).

Saiki et al.. Primer-Directed Enzymatic Amplification of DNA with a Thermostable DNA Polymerase, Science, 239:487-491 (1988).

Sanger et al., Cloning in Single-stranded Bacteriophage as an Aid tp Rapid DNA Sequencing, J. Mol. Biol., 143:161-178 (1980).

Saunders et al., PCR amplification of DNA microdissected from a single polytene chromosome band: a comparison with conventional microcloning, Nucleic Acids Research, 17:9027-9037 (1989).

Steigerwald et al., Ligation-mediated PCR improves the sensitivity of methylation analysis by restriction enzymes and detection of specific DNA strand breaks, Nucleic Acids Research, 18:1435-1439 (1990).

Sterky et al., Direct sequencing of bacterial artifical chromosomes (BACs) and prokaryotic genomes by biotin-capture PCR, Journal of Biotechnology, 60:119-129 (1998).

Strick et al., Stress-Induced Structural Transitions in DNA and Proteins, Annu. Rev. Biophys. Biomol. Struct., 29:523-43 (2000).

Triglia et al., A procedure for in vitro amplification of DNA segments that lie outside the boundaries of known sequences, Nucleic Acids Research, 16:8186 (1988).

Velculescu et al., Serial analysis of gene expression, Science, 270:484-487 (1995).

Walker, Empirical Aspects of Strand Displacement Amplification, PCR Methods Appl.,3:1-6 (1993).

Walker et al., Multiplex strand displacement amplification (SDA) and detection of DNA sequences from *Mycobacterium tuberculosis* and other mycobacteria, Nucleic Acids Research, 22:2670-2677 (1994).

Walker et al., Strand displacement amplification-an isothermal, in vitro DNA amplification technique, Nucleic Acids Research, 20:1691-1696 (1992).

Walter et al., Strand displacement amplification as an in vitro model for rolling-circle replication: Deletion formation and evolution during serial transfer, Proc. Natl. Acad. Sci., 91:7937-7941 (1994).

Westin et al., Anchored multiplex amplification on a microelectronic chip array, Nature Biotechnology, 18:199-204 (2000).

Yershov et al., DNA analysis and diagnostics on oligonucleotide microchips, Proc. Natl. Acad. Sci. USA, 93:4913-4918 (1996).

\* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 1
aatgatacgg cgaccaccga                                               20

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2
caagcagaag acggcatacg a                                             21

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
tcggtggtcg ccgtatcatt                                               20
```

PREPARATION OF NUCLEIC ACID TEMPLATES FOR SOLID PHASE AMPLIFICATION

FIELD OF THE INVENTION

The invention relates to a method of preparing template constructs for solid-phase nucleic acid amplification and to use of the templates in methods of solid-phase nucleic acid amplification.

BACKGROUND

Molecular biology and pharmaceutical drug development now make intensive use of nucleic acid analysis. The most challenging areas are whole genome sequencing, single nucleotide polymorphism detection, screening and gene expression monitoring.

One area of technology which has improved the study of nucleic acids is the development of fabricated arrays of immobilised nucleic acids. These arrays typically consist of a high-density matrix of polynucleotides immobilised onto a solid support material. Fodor et al., Trends in Biotechnology (1994) 12:19-26, describe ways of assembling the nucleic acid arrays using a chemically sensitised glass surface protected by a mask, but exposed at defined areas to allow attachment of suitably modified nucleotides. Typically, these arrays may be described as "many molecule" arrays, as distinct regions are formed on the solid support comprising a high density of one specific type of polynucleotide.

An alternative approach is described by Schena et al., Science (1995) 270:467-470, where samples of DNA are positioned at predetermined sites on a glass microscope slide by robotic micropipetting techniques.

WO 98/44151 and WO 00/18957 both describe methods of forming polynucleotide arrays based on "solid-phase" nucleic acid amplification, which is analogous to a polymerase chain reaction wherein the amplification products are immobilised on a solid support in order to form arrays comprised of nucleic acid clusters or "colonies". Each cluster or colony on such an array is formed from a plurality of identical immobilised polynucleotide strands and a plurality of identical immobilised complementary polynucleotide strands. The arrays so-formed are generally referred to herein as "clustered arrays" and their general features will be further understood by reference to WO 98/44151 or WO 00/18957, the contents of both documents being incorporated herein in their entirety by reference.

As aforesaid, the solid-phase amplification methods of WO 98/44151 and WO 00/18957 are essentially a form of the polymerase chain reaction carried out on a solid support. Like any nucleic acid amplification reaction these methods require the use of forward and reverse amplification primers capable of annealing to a template to be amplified. In the methods of WO 98/44151 and WO 00/18957 both primers are immobilised on the solid support at the 5' end. Other forms of solid-phase amplification are known in which only one primer is immobilised and the other is present in free solution (Mitra, R. D and Church, G. M., Nucleic Acids Research, 1999, Vol. 27, e34; Shendure J, Porreca G. J., Reppas N. B. et al, Science, 2005, Vol. 309, 5741, 1728-1732; Margulies M., Egholm M., Altman W. E. et al, Nature, 2005, 437, 376-380).

In common with all nucleic acid amplification techniques, solid-phase amplification requires the use of forward and reverse amplification primers which include "template-specific" nucleotide sequences which are capable of annealing to sequences in the template to be amplified, or the complement thereof, under the conditions of the annealing steps of the amplification reaction. The sequences in the template to which the primers anneal under conditions of the amplification reaction may be referred to herein as "primer-binding" sequences.

The amplification reaction cannot occur in the absence of annealing of the forward and reverse primers to primer binding sequences in the template to be amplified under the conditions of the annealing steps of the amplification reaction, i.e. if there is insufficient complementarity between primers and template. Some prior knowledge of the sequence of the template is therefore required before one can carry out an amplification reaction to amplify a specific template. The user must usually know the sequence of at least the primer-binding sites in the template in advance so that appropriate primers can be designed, although the remaining sequence of the template may be unknown. The need for prior knowledge of the sequence of the template increases the complexity and cost of solid phase amplification of complex mixtures of templates, such as genomic DNA fragments.

Certain embodiments of the methods described in WO 98/44151 and WO 00/18957 make use of "universal" primers to amplify templates comprising a variable template portion that it is desired to amplify flanked 5' and 3' by common or "universal" primer binding sequences. The "universal" forward and reverse primers include sequences capable of annealing to the "universal" primer binding sequences in the template construct. The variable template or target) portion may itself be of known, unknown or partially known sequence. This approach has the advantage that it is not necessary to design a specific pair of primers for each template to be amplified; the same primers can be used for amplification of different templates provided that each template is modified by addition of the same universal primer-binding sequences to its 5' and 3' ends. The variable template sequence can therefore be any DNA fragment of interest. An analogous approach can be used to amplify a mixture of templates, such as a plurality or library of template nucleic acid molecules (e.g. genomic DNA fragments), using a single pair of universal forward and reverse primers, provided that each template molecule in the mixture is modified by the addition of the same universal primer-binding sequences.

Such "universal primer" approaches to solid-phase amplification are advantageous since they enable multiple template molecules of the same or different, known or unknown sequence to be amplified in a single amplification reaction on a solid support bearing "universal" forward and reverse primers.

The drawback of the standard "universal primer" approach is that hitherto it has been necessary to carry out several solution phase ligation reaction and purification steps on the targets in order to prepare the target-adaptor (or template) constructs suitable for amplification using the universal forward and reverse primers. Suitable template constructs, or libraries of template constructs, to be amplified with universal primers must be prepared by modifying the target polynucleotides that it is desired to amplify by addition of known adaptor sequences to the 5' and 3' ends of the target molecule(s). The target molecules themselves may be any polynucleotide molecules it is desired to amplify (e.g. random fragments of human genomic DNA). The adaptors are typically short oligonucleotides that may be synthesised by conventional means. The adaptors are usually attached to the 5' and 3' ends of target nucleic acid fragments by ligation in solution phase, prior to attachment of the template to a solid support, or by sub-cloning of the target into a vector at a cloning site that is flanked by suitable adaptor sequences.

All of the known template preparation methods require solution-phase reaction steps, after which the prepared template must be immobilised on a solid support such that solid-phase amplification can proceed.

The present inventors now describe a method of directly preparing template constructs for solid-phase amplification that reduces or removes the need for solution phase ligation reaction steps. The method involves the use of a ligation reaction to directly attach a first end of an unmodified target polynucleotide to the adaptor constructs immobilised on a solid support. The second end of the target polynucleotide can undergo a ligation reaction once immobilised, or can have been treated prior to the ligation of the first end. The method produces template construct(s) immobilised on a solid support that can subsequently be amplified by solid-phase amplification using multiple copies of a single primer-pair, or even a single primer. The method of the invention is applicable to whole-genome amplification as well as mono-template amplifications.

SUMMARY OF THE INVENTION

In a first aspect the invention provides a method of preparing template constructs for solid-phase nucleic acid amplification which comprises performing the following ligation reactions a) and b):
a) a ligation reaction in which the first end of one or more target polynucleotide molecules are ligated to surface-bound adaptor polynucleotide molecules; and
b) a ligation reaction in which solution-phase adaptor polynucleotide molecules are ligated to the second end of said target polynucleotide molecules;
thereby producing one or more template constructs attached to a solid support, wherein each of said template constructs comprises a target polynucleotide molecule ligated to a surface-bound adaptor polynucleotide molecule and a solution-phase polynucleotide molecule.

Ligation reaction (a) typically involves ligation of one or more target polynucleotide molecules to surface-bound adaptor polynucleotide molecules attached to a solid support such the 5' end of one strand of each individual template polynucleotide molecule is joined in phosphodiester linkage to the 3' end of a strand of a surface-bound adaptor polynucleotide molecule, this strand of the adaptor being attached to the solid support at or near the 5' end.

Ligation reaction (b) typically involves ligation of solution-phase adaptor polynucleotide molecules to the target polynucleotide molecules such that at least one strand of a solution-phase adaptor polynucleotide molecule is joined in phosphodiester linkage to at least one strand of each individual target polynucleotide molecule.

In a preferred embodiment of the method ligation reaction a) is carried out before ligation reaction b).

In a second aspect the invention provides a method of amplifying nucleic acid templates by solid-phase nucleic acid amplification comprising:
preparing templates constructs for solid-phase amplification using the method according to the first aspect of the invention and carrying out a nucleic acid amplification reaction wherein said template constructs are amplified using forward and reverse amplification primers.

In a further aspect the invention relates to use of the method according to the second aspect of the invention or the amplified products of said method for providing nucleic acid molecules for sequencing, re-sequencing, gene expression monitoring, genetic diversity profiling, diagnosis, screening, whole genome sequencing, scoring or discovery of single nucleotide polymorphisms, or any other applications involving the amplification of nucleic acids or the sequencing thereof.

In a still further aspect the invention provides a method of nucleic acid sequencing which comprises amplifying one or more nucleic acid template constructs prepared according to the first aspect of the invention and carrying out a sequencing reaction to determine the sequence of the whole or a part of at least one amplified nucleic acid strand produced in the amplification reaction.

BRIEF DESCRIPTION OF THE DRAWINGS

FIG. 2 illustrates the results of solid-phase amplification reactions carried out following solid-phase "ligation" reactions in the presence of different combinations of reagents.

DETAILED DESCRIPTION OF THE INVENTION

Figure 1:
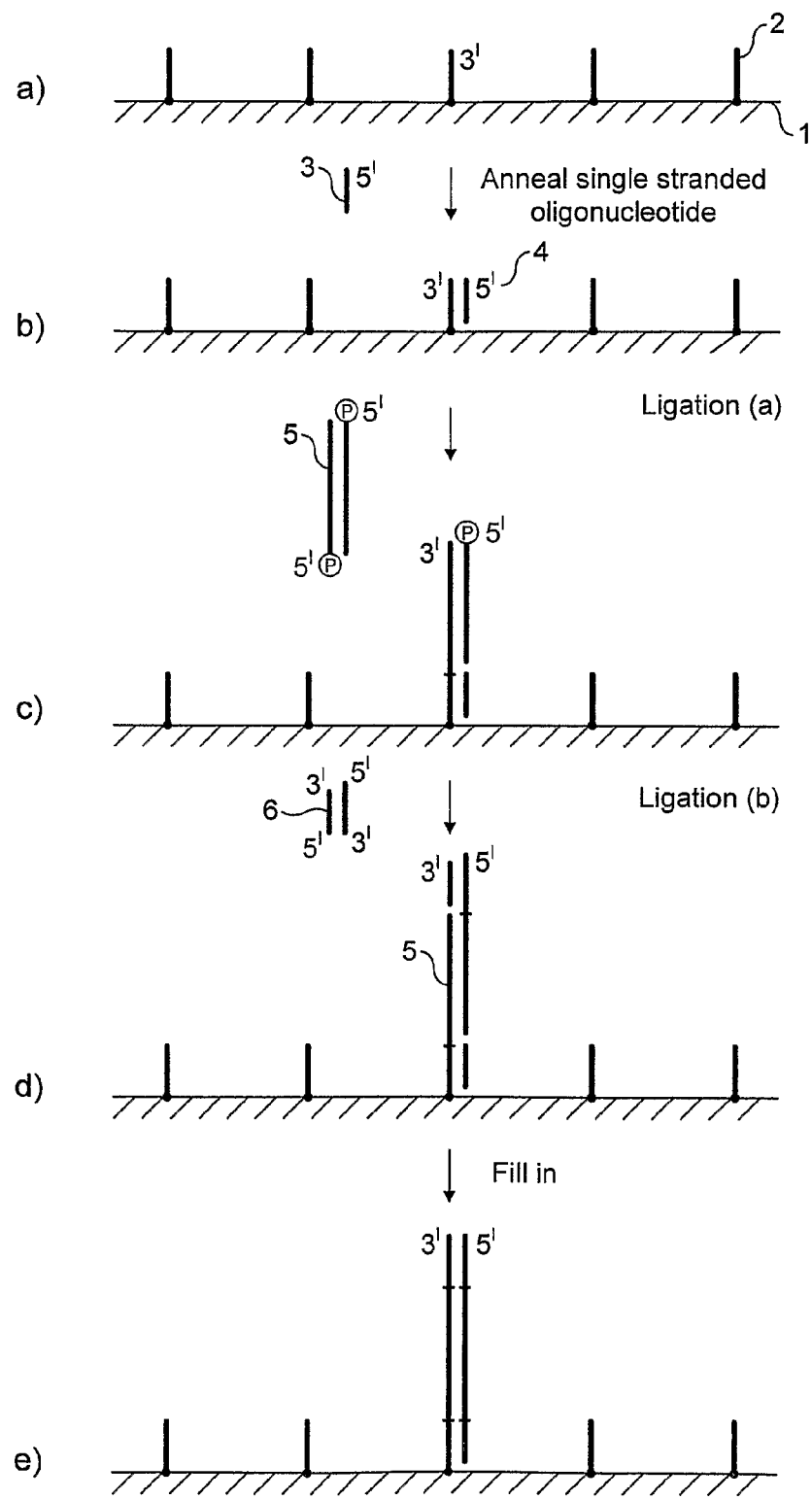
FIG. 1 is a schematic illustration of one embodiment of the method according to the first aspect of the invention, based on use of double-stranded polynucleotide templates.

In its first aspect the invention relates to a method of preparing template constructs for solid-phase nucleic acid amplification which comprises two distinct ligation reactions. It is an essential feature of the method that one of the ligation reactions takes place on a solid support, i.e. it results in the joining of two polynucleotide molecules, one of which is already attached to a solid support.

The method as a whole results in the formation of a template construct which comprises a target molecule that it is desired to amplify, modified by the addition of adaptor sequences to its 5' and 3' ends. A key feature of the method is that it leads to formation of a template construct which is already attached to a solid support, ready for solid-phase amplification. The method of the invention thus avoids the complexity and cost of prior art methods which require separate steps in order to modify a template by addition of adaptor sequences and subsequently attach the resultant template construct to a support ready for solid-phase amplification.

As used herein the terms "nucleic acid template construct" or "template construct" refer to a nucleic acid construct which is formed by ligation of adaptors to the 5' and 3' ends of a target molecule in the method of the invention. The template construct thus comprises a target polynucleotide sequence that it is desired to amplify in a solid-phase nucleic acid amplification reaction flanked 5' and 3' by adaptor polynucleotide sequences. Template constructs thus have the general structure:
5'-adaptor sequence-target sequence-adaptor sequence-3'

The adaptor sequences (derived from the adaptor molecules ligated to a target molecule in the method of the invention) will include primer-binding sequences required for solid-phase amplification. The target sequence can be any sequence that it is desired to amplify and may be known, unknown or partially known. In the case of the ligation reaction performed in solution, the adaptor sequence can be longer than the primer binding sequence (such that the amplification primers are shorter than the adaptors). In the case of the solid phase ligation reaction, the adaptor sequence and primer sequence may be exactly the same (i.e. the ligation can attach the target directly to the reverse amplification primer), or the adaptor sequence may be longer than the primer binding sequence if both the adaptor and a reverse amplification primer containing fewer bases than the adaptor at the 3'-end are both attached to the surface.

In the case of solid-phase amplification using forward and reverse amplification primers to amplify a template construct, the template construct must include (when viewed as a single strand) at the 3' end an adaptor-derived sequence comprising a primer-binding sequence which is capable of annealing to the forward amplification primer, a target sequence that it is desired to amplify, and at the 5' end an adaptor-derived sequence comprising a primer-binding sequence, the complement of which is capable of annealing to the reverse amplification primer (i.e. the 5'-end of the template contains the same bases as the reverse amplification primer). In this context, the "forward" primer will be that which anneals to the free 3' end of the immobilised template construct and is extended in the first amplification cycle, and the copy of the molecule produced in the first amplification cycle is capable of hybridising to the reverse amplification primer.

It will be appreciated, however, that the template construct to be amplified will commonly be in double-stranded form, in which case the complementary strand includes at the 3' end an adaptor-derived sequence comprising a primer-binding sequence capable of annealing to the reverse amplification primer and at the 5' end an adaptor-derived sequence comprising a primer-binding sequence the complement of which is capable of annealing to the forward amplification primer.

The term "annealing" as used in this context to describe specific hybridisation under the conditions to be used for the annealing steps of the amplification reaction. The conditions encountered during the annealing steps of a solid-phase amplification reaction will be generally known to one skilled in the art, although the precise annealing conditions will vary from reaction to reaction. Typically such conditions may comprise, but are not limited to, (following a denaturing step at a temperature of about 94° C. for about one minute) exposure to a temperature in the range of from 40° C. to 72° C., more specifically 50° C. to 65° C., and still more specifically 55-58° C. for a period of about 1 minute in standard amplification reaction buffer, (optionally supplemented with 1M betain and 1.3% DMSO). It will be appreciated that 100% complementarity between the primer binding sequences and the amplification primers is not absolutely required for annealing under such conditions, although it is generally preferred. It is also possible to amplify the nucleic acid strands isothermally, where the denaturation steps are carried out at the same temperature as the extension steps. Examples of method used in the isothermal amplification of clusters are detailed in WO0246456, which is incorporated herein in its entirety by reference.

The term "target polynucleotide molecule" is used to refer to a polynucleotide molecule that it is desired to be able to amplify by solid-phase amplification. The target polynucleotide molecule is modified by the addition of adaptor sequences to its 5' and 3' ends in the method of the invention in order to produce a template construct ready for amplification. Thus, the "target polynucleotide molecule" corresponds to the variable portion in the template construct but lacks the universal adaptor sequences.

In the various embodiments of the method of the invention the "target polynucleotide molecule" may be a fully or partially double-stranded polynucleotide molecule. The precise sequence of the target molecule is not material to the invention. Generally the target molecule will be a DNA molecule. Modified DNA molecules including non-natural nucleotides and/or non-natural backbone linkages could be used as the target, provided that the modifications do not preclude copying in a nucleic acid amplification reaction. The target nucleic acid may be fragmented, for example using nebulisation, hydrodynamic shearing, sonication or enzyme treatment, prior to ligation of the adaptors, and thus the terms "target" and "target fragments" are used interchangeably.

The method of the invention may be applied to multiple copies of the same target molecule (so-called monotemplate applications) or to a mixture of different target molecules which differ from each other with respect to nucleotide sequence over all or a part of their length. In one embodiment the method can be applied to a library of nucleic acid target molecules, such that common or "universal" adaptor molecules are added to the 5' or 3' ends of each of the individual target molecules in the library to produce a library of template constructs. The resulting library of template constructs may subsequently be amplified using a pair of common or "universal" forward and reverse primers which are capable of annealing to "universal" primer binding sequences in the adaptors.

The "library" of target molecules may be a plurality of target molecules derived from a common source, for example a library of genomic DNA fragments derived from a particular individual. In a preferred embodiment the library will comprise random fragments of human genomic DNA. The library may be derived from a whole genome or from part of a genome (e.g. a single chromosome or sub-fraction thereof). The library may contain genomic fragments derived from one individual or several individuals.

As aforesaid, the method of preparing template constructs according to the first aspect of the invention requires two ligation reactions as follows:

a) a ligation reaction in which the first end of one or more target polynucleotide molecules are ligated to surface-bound adaptor polynucleotide molecules; and b) a ligation reaction in which solution-phase adaptor polynucleotide molecules are ligated to the second end of said target polynucleotide molecules.

Each ligation reaction requires joining of at least one polynucleotide strand to another polynucleotide strand. In this context "joining" means covalent linkage of two polynucleotide strands which were not previously covalently linked. Preferably such "joining" will take place by formation of a phosphodiester linkage between the two polynucleotide strands but other means of covalent linkage (e.g. non-phosphodiester backbone linkages) may be used. However, it is an essential requirement that the covalent linkages formed in the ligation reactions allow for read-through of a polymerase, such that the resultant construct can be copied in a nucleic acid amplification reaction using primers which binding to sequences in the regions of the template construct that are derived from the adaptor molecules.

The ligation reactions will preferably be enzyme-catalysed. The nature of the ligase enzyme used for enzymatic ligation is not particularly limited. Non-enzymatic ligation techniques (e.g. chemical ligation) may also be used, again provided that the non-enzymatic ligation leads to the formation of a covalent linkage which allows read-through of a polymerase, such that the resultant construct can be copied in a nucleic acid amplification reaction.

In the various embodiments of the method of the invention the ligation reactions may involve joining of two double-stranded polynucleotide molecules such that covalent linkages are formed between both strands of the two double-stranded molecules, or may involve joining of two double-stranded polynucleotide molecules such that one strand of one of the double-stranded molecules is covalently linked to one strand of the other double-stranded molecule.

The adaptor molecules added in the ligation reactions may be fully or partially double-stranded polynucleotide molecules generally referred to herein as "adaptor duplexes".

The adaptor duplexes must contain primer-binding sequences which enable specific annealing of amplification primers when the template constructs into which the adaptors are incorporated are used in an amplification reaction. The precise nucleotide sequence of the primer-binding sequences is not limiting to the invention, and is determined by the sequence of the primers to be used in the amplification reaction. The sequence of the primers will in turn generally be selected to avoid or minimise binding of the primer to the target portion of the template construct under the conditions of the amplification reaction, but is otherwise not particularly limited.

The length of the primer-binding sequence in each adaptor is also not particularly limited but will typically be between 20 and 100 nucleotides, more preferably between 20 and 50 nucleotides and still more preferably between 20 and 35 nucleotides. The adaptors may include further nucleotide sequences in addition to the primer-binding sequences. By way of example, the adaptors may include tag sequences, which can be used to tag or mark template molecules derived from a particular source. The general features and use of such tag sequences is described in the applicant's pending application published as WO 05/068656. In other embodiments the adaptors may include additional sequences which provide a binding site for a sequencing primer to initiate a subsequent nucleic acid sequencing reaction.

The structure of the adaptors must be such that primers annealing to the primer-binding sequences can be extended by addition of nucleotides at the 3' end to permit copying of the target portion of the template construct in the amplification reaction. Thus, the adaptors cannot contain any moiety which prevents the polymerase to be used for the amplification reaction from "reading-through" into the target sequence. Outside of these constraints the precise structure of the adaptor molecules is not particularly limited. The adaptors may contain non-natural nucleotides, non-natural backbone linkages, non-nucleotide chemical moieties or any combination thereof, provided that such features do not prevent primer-binding and subsequent primer extension. The adaptors to be attached to a solid surface may include non-nucleotide chemical moieties to enable such attachment. For example, they may include a thiophosphate or phosphorothioate group or an amino group at the 5' end of a polynucleotide strand in order to enable covalent attachment to a suitably functionalised solid support.

The method of the invention requires two adaptor duplexes, referred to as the "surface bound adaptor" and the "solution phase adaptor". The general features of the two types of adaptors are as described above and are generally similar, except that the surface bound adaptor must be capable of being attached to a solid support and may therefore include specific features or modifications to permit such attachment.

The term "solid support", as used herein, refers to the material to which the surface-bound adaptors (and amplification primers required for subsequent solid-phase amplification) are attached. Suitable solid supports are available commercially, and will be apparent to the skilled person. The supports can be manufactured from materials such as glass, ceramics, silica and silicon. Supports with a gold surface may also be used. The support may comprise a flat (planar) surface, or at least a structure in which the surface-bound adaptors are attached in approximately the same plane. In other embodiments, the solid support may be non-planar and may even be formed from a plurality of discrete units, e.g. microbeads. The beads may be present at such a concentration to ensure a significant percentage of the beads only ligate to a single target molecule, and the beads can be amplified in an emulsion to ensure each bead contains multiple copies of the same single target. Supports of any suitable size may be used. For example, planar supports might be on the order of 1-10 cm in each direction. Preferred supports include, but are not limited to, solid-supported polyacrylamide hydrogels, particularly those described in WO 2005/065814, the contents of which are incorporated herein in their entirety by reference.

When referring to attachment or immobilisation of molecules (particularly nucleic acids such as adaptors, amplification primers etc.) to a solid support, the terms "immobilised" and "attached" are used interchangeably and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. surface-bound adaptors or amplification primers) remain immobilised or attached to the support under the conditions in which it is intended to use the support, for example during ligation reaction (a) and subsequent applications requiring nucleic acid amplification and/or sequencing.

Certain embodiments of the invention make use of solid supports comprised of an inert substrate or matrix (e.g. glass slides, glass or polymer beads etc) which is been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

The "surface-bound adaptor" is so-called because it must be attached to a solid support prior to ligation reaction a). Attachment to the solid support must involve linkage of at least one strand of the surface bound adaptor to the support. If the surface bound adaptor is single-stranded it will generally be attached to the solid support at or near the 5' end, leaving the 3' end free for ligation to a 5' phosphate group on one strand of a template polynucleotide. If the surface-bound adaptor is a duplex then generally only one strand will be attached to the solid support, again at or near the 5' end leaving the 3' end of this same strand free for ligation to a template molecule. The complementary strand of the duplex will generally not be directly attached to the solid support, but will be held by hybridisation to the strand that is attached to the support.

The "solution-phase adaptor" is so-called because it is added as reagent in free solution to ligation reaction b). The target molecule to which the solution phase adaptor is joined in ligation reaction b) may itself be added to the ligation reaction as a reagent in free solution but will preferable already be attached to a solid support via a surface-bound adaptor. Thus, in preferred embodiments of the invention ligation reaction a) is carried out before ligation reaction b).

As aforesaid, the adaptors used in the method of the invention may be fully or partially double-stranded polynucleotide molecules. Depending on the nature of the ligation reaction, double-stranded adaptor molecules may be blunt ended or may include overhangs of one or more nucleotides at one or both ends. In one embodiment such overhangs may be a short stretch of nucleotides of defined sequence forming a cohesive or "sticky" end which facilitates ligation to target polynucleotides having a complementary sticky end. Sticky ends are typically generated by digestion with a restriction endonuclease. In other embodiments the overhang may be a single nucleotide. Single nucleotide overhangs can be easily generated by enzymatic addition of a single nucleotide to a blunt ended molecule, for example using Taq or klenow exo minus polymerase.

The individual polynucleotide strands of the adaptor molecules may be phosphorylated at the 5' end or non-phosphorylated and may include other non-nucleotide chemical modifications at the 5' end (e.g. biotinylation).

In certain embodiments of the invention the surface-bound adaptor molecule may comprise an amplification primer attached to the solid support. In a preferred embodiment surface-bound adaptor duplexes may be formed by annealing single-stranded oligonucleotides to amplification primers which are already attached to a solid support.

Non-limiting specific embodiments of the method of the invention will now be described in further detail with reference to the accompanying drawings. Features described as being preferred in relation to one specific embodiment of the invention apply mutatis mutandis to other specific embodiments of the invention unless stated otherwise.

FIG. 1 is a schematic illustration of one embodiment of a method according to the invention which is based on ligation of surface-bound and solution-phase adaptor duplexes to a double-stranded template polynucleotide to form a template construct attached to a solid support.

The starting material in FIG. 1(a) is a solid support 1 of a type generally known in the art. The solid support is shown as substantially planar but other supports such as microbeads etc. could be used. A plurality of amplification primers 2 are covalently attached to the solid support at or near their 5' ends, leaving the 3' ends of the primers free for primer extension. Amplification primers are generally single-stranded polynucleotide structures. They may contain a mixture of natural and non-natural bases and also natural and non-natural backbone linkages, provided that any non-natural modifications do not preclude function as a "primer", that being defined as the ability to anneal to a template polynucleotide strand during the conditions of a nucleic acid amplification reaction and act as an initiation point for synthesis of a new polynucleotide strand complementary to a template strand.

Amplification primers may additionally comprise non-nucleotide chemical modifications, again provided that such modifications do not prevent "primer" function. Chemical modifications may, for example, facilitate covalent attachment of the primer to a solid support. Certain chemical modifications may themselves improve the function of the molecule as a primer, or may provide some other useful functionality, such as for example providing a site for cleavage to enable the primer (or an extended polynucleotide strand derived therefrom) to be cleaved from the solid support The precise sequence of the amplification primers is generally not material to the invention but will be determined by the requirements of the solid-phase amplification reaction be carried out on the solid support. Typically a mixture of substantially equal amounts of one type of forward amplification primer and one type of reverse amplification primer (of different sequence to the forward primer) will be attached to the surface. In other embodiments the forward and reverse primers attached to the surface may in fact be of identical-sequence. Still further embodiments could involve the use of several different primer-pairs on a single support. Covalent attachment or "grafting" of primers onto the solid support may be carried out using techniques generally known in the art (described for example in WO 9844151, WO 0018957, WO05030695 and WO 05065814).

In order to form surface-bound adaptors for the first ligation reaction single-stranded oligonucleotides are hybridised to a subset of the amplification primers attached to the solid support to form surface-bound adaptor duplexes. The single-stranded oligonucleotides will typically be synthetic oligonucleotides and may include or lack 5' phosphate groups. For simplicity only a single surface-bound adaptor duplex is shown in FIG. 1(b). Conditions for hybridisation of single-stranded oligonucleotides to surface-bound primers in order to form the surface-bound adaptor duplexes will generally be well known to persons skilled in the art. In order to form an array suitable for amplification, the density of ligation should be controlled to enable attachment at a surface density capable of individual resolution of the separate single molecules. Such densities are limited by the optical resolution of the imaging system, but for a typical wide field imaging device (such as an optical microscope) will be at a density of less than one molecule per 250 nm by 250 nm, or approximately $10^7$ molecules per $mm^2$. A typical density of ligated single molecules will be between $10^4$ to $10^6$ molecules per $mm^2$.

In order to provide a surface which will support subsequent solid-phase amplification it is important that only a portion of the adaptor duplexes undergo ligation, leaving an excess of single-stranded primers on the surface. This can be controlled by using a dilute solution of the target strands; typically less than 100 pM concentration. In embodiments such as that illustrated in FIG. 1, the density and spacing of adaptor duplexes on the surface can also be controlled by adjusting the amount and concentration of single-stranded oligonucleotides allowed to hybridise to primers attached to the support, such that the resulting adaptor duplexes (and the template constructs subsequently attached thereto) are fairly evenly spaced on the support and surrounded by an excess of "free" primers. In an alternative embodiment, the adaptor sequence can be longer than the amplification primer sequence, as long as the sequence at the 5'-end of both species is identical, to ensure hybridisation during amplification. Design of a suitable single stranded oligonucleotide can ensure hybridisation to solely the dilute adaptor primer rather than the excess of the shorter amplification primer. In a typical experiment the total density of primers on the solid support will be at least 1 $fmol/mm^2$, preferably at least 10 $fmol/mm^2$.

In an alternative embodiment (not illustrated) the surface-bound adaptor duplexes may be pre-formed in solution by hybridisation of two complementary oligonucleotides and then attached to the solid support. If the adaptor is pre-formed in solution, the step of attaching the adaptor duplexes to the surface may be carried before, after or at the same time as attachment of the amplification primers required for the subsequent solid-phase amplification reaction. If the adaptors are pre-formed in solution and subsequently attached to the surface it is again important to ensure that an excess of unhybridised amplification primers is attached to the surface to support the subsequent solid-phase amplification.

Once the surface-bound adaptor duplexes are formed on the solid support, a double-stranded target polynucleotide molecule can be joined to each of the surface-bound adaptors in ligation reaction (a). For simplicity only a single ligation event with a single target molecule is shown in FIG. 1. However, it will be appreciated that in practical embodiments the ligation reaction will usually contain a plurality of target molecules and the solid support will bear multiple surface-bound adaptors. For monotemplate applications multiple copies of a single target molecule will be added to the ligation reaction, whereas in other embodiments a mixture of different target molecules may be added to the ligation reaction, for example a mixture of random genomic DNA fragments. In the latter case a different target molecule may be added to each surface-bound duplex on the solid support. Subsequent solid-phase amplification will thus produce a clustered array wherein each individual cluster or colony on the array is derived from amplification of a different template molecule.

Each target molecule added to the ligation reaction is typically phosphorylated at both 5' ends and may be blunt ended, in which case the surface-bound adaptor may also be blunt ended, at least at the end not attached to the solid-surface. In other embodiments the target molecules and surface-bound adaptors may have complementary sticky ends generated by restriction enzyme digestion. In the illustrated embodiment both target molecule 5 and adaptor duplex 4 are blunt ended. However, due to the lack of 5' phosphate on the adaptor duplex only one strand of the target is covalently joined to the adaptor in the ligation reaction, via phosphodiester linkage between the free 3' hydroxyl group on the adaptor and a 5' phosphate on one strand of the target. As is shown, the strand of the adaptor duplex to which the target is joined by formation of a phosphodiester linkage in ligation reaction (a) is the same strand as is attached to the solid support.

If the target molecule 5 is blunt ended, then it may be ligated to the surface-bound adaptor in either orientation. In most embodiments, and particularly when the target is a polynucleotide of unknown sequence such as a random genomic fragment, it is generally not necessary to control the direction of this ligation such that the target is attached in a particular orientation. Ligation reaction (a) can be catalysed by any suitable ligase enzyme having specificity for double-stranded polynucleotides (e.g. T4 DNA ligase).

When ligation reaction (a) is complete the support shown in FIG. 1(c) may be washed to remove excess ligase, buffers and any unligated target polynucleotides.

Ligation reaction (b) is then carried out in which a solution phase adaptor duplex 6 is joined to the free second end of each target polynucleotide molecule 5 now attached to the support via the surface-bound adaptor. In the illustrated embodiment the solution phase adaptor duplex 6 is blunt ended at the end which will be joined to the target polynucleotide but includes a short 5' overhang of at least one nucleotide at the other end. Inclusion of such an overhang provides a means to control the directionality of the ligation reaction such that the solution-phase adaptor 6 is joined to the target 5 in a particular orientation. It may be important to control the orientation of the adaptor in this ligation reaction to ensure that the correct combination of primer-binding sequences are added to the target, such that it may be amplified in a solid-phase amplification reaction. Other means of controlling directionality of the ligation reaction include the addition of blocking groups to one end of the adaptor (which may be denoted the "non-ligatable" end). Typically such modifications will be 5' modifications on one strand of the adaptor, and may comprise the addition of a chemical blocking group for example biotin.

In the embodiment illustrated the solution-phase adaptor duplex 6 is formed from complementary polynucleotide strands that lack 5' phosphate groups (e.g. chemically synthesised oligonucleotides). Thus, ligation reaction (b) results in joining of only one strand of the adaptor duplex 6 to one strand of the target polynucleotide 5 via phosphodiester linkage between the free 5' phosphate on target 5 and the free 3' hydroxyl group at the blunt end of the adaptor duplex 6. Ligation reaction (b) may also be catalysed by any suitable ligase enzyme having specificity for double-stranded polynucleotides.

The resulting product shown schematically in FIG. 1(d) includes two nicks formed where the 3' ends of the template polynucleotide 5 abut the non-phosphorylated 5' ends of the surface-bound and solution phase duplexes (4, 6). As a final step in the formation of the template constructs these nicks may be filled in by methods generally known in the art, for example by action of a polymerase enzyme capable of extending the template from its 3' ends (e.g. Bst polymerase).

In other embodiments of the method (not illustrated) both the surface-bound and solution-phase adaptor duplexes may have phosphorylated 5' ends. In such embodiments both strands of the surface-bound adaptor will be joined to target strands in ligation reaction (a) and both strands of the solution-phase adaptor will be joined to target strands in ligation reaction (b), and the "filling in" step is not required. In such embodiments side-products can potentially be formed by ligation of the surface-bound and solution-phase adaptor molecules. Ligation of surface-bound and solution-phase adaptors can be minimised by using an excess of target in ligation reaction (a) to ensure that all available surface-bound adaptors are joined to templates in this ligation reaction. The excess unbound targets should then be removed prior to ligation reaction (b). Alternatively, formation of the side-products can be avoided by engineering the surface-bound and solution-phase adaptors to each contain half of a restriction enzyme recognition site, such that the full site is formed only when the two adaptors are ligated together. Inclusion of the appropriate restriction enzyme during the ligation reaction will ensure that any complexes formed by ligation of the surface-bound and solution-phase adaptors are cleaved as soon as they are formed.

In the foregoing embodiments the surface-bound and solid-phase adaptor duplexes may be of different sequence or may be identical in sequence, depending on the form of the subsequent solid-phase amplification reaction.

The end products of this method, schematically illustrated in FIG. 1(e), are double-stranded template constructs comprised of a surface-bound adaptor 4, a target molecule 5 and a solution-phase adaptor 6, covalently joined such that the adaptors flank the target molecule. One strand only of the template construct is attached to the solid support at the 5' end. For simplicity only a single template construct is shown in FIG. 1, whereas in a typical embodiment many such constructs (typically in the range of from $10^4/mm^2$ to $10^7/mm^2$) will be immobilised on the support at a fairly even spacing and surrounded by an excess of amplification primers, ready for solid-phase amplification.

If a mixture of target molecules of different sequence (e.g. a library of genomic DNA fragments) is added to ligation reaction (a), each (or at least a majority) of the template constructs formed on the solid support will comprise a different target sequence, flanked by common or universal adaptor sequences. Subsequent solid-phase amplification using corresponding universal primers will result in the formation of a clustered array wherein each individual colony or cluster on the array is derived from amplification of a different template.

Solid-Phase Amplification

Once formed, template constructs prepared according to the methods described above can be used for solid-phase nucleic acid amplification.

Thus, in further aspects the invention provides a method of amplifying nucleic acid template constructs by solid-phase amplification comprising:

preparing template constructs for solid-phase amplification comprising one or more templates to be amplified using the method according to the first aspect of the invention and carrying out a nucleic acid amplification reaction wherein said templates are amplified.

The term "solid-phase amplification" as used herein refers to any nucleic acid amplification reaction carried out on or in association with a solid support such that all or a portion of the amplified products are immobilised on the solid support as they are formed. In particular, the term encompasses solid-phase polymerase chain reaction (solid-phase PCR), which is a reaction analogous to standard solution phase PCR, except that one or both of the forward and reverse amplification primers is/are immobilised on the solid support. The method also covers isothermal methods, where the denaturation and extension reactions of the amplification are carried out at the same temperature.

Although the invention encompasses "solid-phase" amplification methods in which only one amplification primer is immobilised (the other primer usually being present in free solution), it is preferred for the solid support to be provided with both the forward and the reverse primers immobilised. In practice, there will be a "plurality" of identical forward primers and/or a "plurality" of identical reverse primers immobilised on the solid support, since the amplification process requires an excess of primers to sustain amplification. References herein to forward and reverse primers are to be interpreted accordingly as encompassing a "plurality" of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In other embodiments of the invention the forward and reverse primers may contain template-specific portions of different sequence.

In certain embodiments, two types of forward primers differing in some property may be used in conjunction with a single reverse primer (or vice versa). It is also possible to carry out "multiplex" PCR, in which two or more sets of forward and reverse primers are used to amplify two or more templates in parallel in a single reaction. All of these variations of the basic amplification reaction are contemplated by the invention in the context of "solid-phase" amplification.

In all embodiments of the invention, amplification primers are preferably immobilised by covalent attachment to the solid support at or near the 5' end of the primer, leaving the template-specific portion of the primer free for annealing to it's cognate template and the 3' hydroxyl group free for primer extension. Any suitable covalent attachment means known in the art may be used for this purpose. The chosen attachment chemistry will depend on the nature of the solid support, and any derivatisation or functionalisation applied to it. The primer itself may include a moiety, which may be a non-nucleotide chemical modification, to facilitate attachment. In one particularly preferred embodiment the primer may include a sulphur-containing nucleophile, such as phosphorothioate or thiophosphate, at the 5' end. In the case of solid-supported polyacrylamide hydrogels (as described below), this nucleophile will bind to a bromoacetamide group present in the hydrogel. The most preferred means of attaching primers and templates to a solid support is via 5' phosphorothioate attachment to a hydrogel comprised of polymerised acrylamide and N-(5-bromoacetamidylpentyl) acrylamide (BRAPA).

It is preferred to use the template constructs prepared according to the first aspect of the invention to prepare clustered arrays of nucleic acid colonies, analogous to those described in WO 0018957, WO 9844151, WO 05065814 or WO05030695 by solid-phase amplification. The terms "cluster" and "colony" are used interchangeably herein to refer to a discrete site on a solid support comprised of a plurality of identical immobilised nucleic acid strands and a plurality of identical immobilised complementary nucleic acid strands. The term "clustered array" refers to an array formed from such clusters or colonies. In this context the term "array" is not to be understood as requiring an ordered arrangement of clusters.

Use in Sequencing/Methods of Sequencing

The invention also encompasses methods of sequencing amplified nucleic acids generated by solid-phase amplification. Thus, the invention provides a method of nucleic acid sequencing comprising amplifying one or more nucleic acid template constructs using a method as described above and carrying out a nucleic acid sequencing reaction to determine the sequence of the whole or a part of at least one amplified nucleic acid strand produced in the amplification reaction.

Any suitable method for of sequencing may be used to determine a sequence read of the immobilised enriched targets. Suitable methods of sequencing include the use of sequencing by addition of nucleotide bases, for example sequencing by synthesis (SBS) using nucleoside triphosphates (as described in WO04018497) and DNA polymerases, or using oligonucleotide cassettes and ligases; as described in U.S. Pat. No. 6,306,597 or Science, 309:5741, 1728-1732 (2005). The enriched targets may also be sequenced by pyrosequencing (Nature. 437:376-380 (2005)), or by MPSS where the strands are degraded rather than extended (Nat Biotechnol. 6:630-6344 (2000)).

In "sequencing by synthesis" or SBS a new polynucleotide strand based-paired to a template strand is built up in the 5' to 3' direction by successive incorporation of individual nucleotides complementary to the template strand. In one embodiment of SBS the substrate nucleoside triphosphates used in the sequencing reaction are each labelled on the base with different labels permitting determination of the identity of the incorporated nucleotide as successive nucleotides are added. The labelled nucleoside triphosphates also have a 3' blocking group which prevents further incorporation of complementary bases by the polymerase. The label of the incorporated base can then be determined and the blocking group removed to allow further polymerisation to occur.

The initiation point for the sequencing reaction may be provided by annealing of a sequencing primer to a product of the solid-phase amplification reaction. In this connection, one or both of the adaptors added during formation of the template construct may include a nucleotide sequence which permits annealing of a sequencing primer to amplified products derived by amplification of the template construct. The ligation step b, using adaptors in solution is more amenable to adding a sequence longer than the amplification primer sequence, but this can be performed during ligation step a if desired.

The products of solid-phase amplification reactions wherein both forward and reverse amplification primers are covalently immobilised on the solid surface are so-called "bridged" structures formed by annealing of pairs of immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing it is preferred to remove substantially all or at least a portion of one of the immobilised strands in the "bridged" structure in order to generate a template which is at least partially single-stranded. The portion of the template which is single-stranded will thus be available for hybridisation to a sequencing primer. The process of removing all or a portion of one immobilised strand in a "bridged" double-stranded nucleic acid structure may be referred to herein as "linearization".

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage, cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the amplification reaction is performed with only one primer covalently immobilised and the other in free solution.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example hydroxide or formamide solution will be apparent to the skilled reader with reference to standard molecular biology protocols (Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.)

Denaturation results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearised amplification product, sequentially incorporating one or more nucleotides into a polynucleotide strand complementary to the region of amplified target strand to be sequenced, identifying the base present in one or more of the incorporated nucleotide(s) and thereby determining the sequence of a region of the target strand.

One preferred sequencing method which can be used in accordance with the invention relies on the use of modified nucleotides that can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA target. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label. However the detectable label need not be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means.

The methods of the invention are not limited to use of the sequencing method outlined above, but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing) and sequencing by ligation-based methods.

The target polynucleotide to be sequenced using the method of the invention may be any polynucleotide that it is desired to sequence. Using the template preparation method described in detail herein it is possible to prepare template constructs starting from essentially any double or single-stranded target polynucleotide of known, unknown or partially known sequence. With the use of clustered arrays prepared by solid-phase amplification it is possible to sequence multiple targets of the same or different sequence in parallel.

The invention will be further understood with reference to the following experimental example:

EXAMPLE

Solid-phase amplification was carried out in 8 channel glass chips such as those provided by Micronit (Twente, Nederland) or IMT (Neuchâtel, Switzerland) coated with aminopropyltriethoxysilane derivatised with 1,3,5-benzenetriacetic acid (BTA). The experimental conditions and procedures are readily applicable to other solid supports.

The reaction steps of the coating procedure as follows:

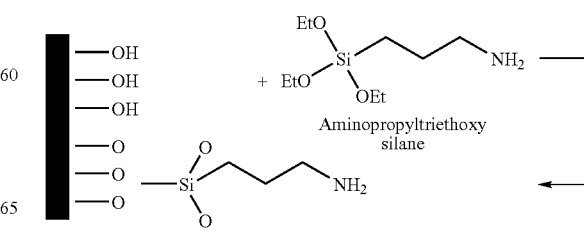

Step 1: Conversion of Glass to Amine-Terminated Glass

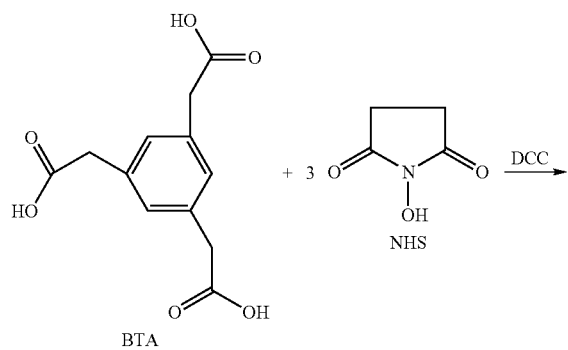

BTA + 3 NHS → (DCC)

Step 2: Preparation of Active Ester

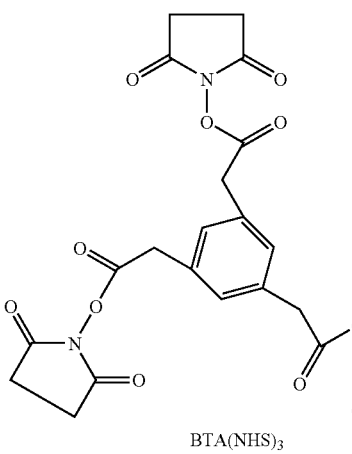

BTA(NHS)₃

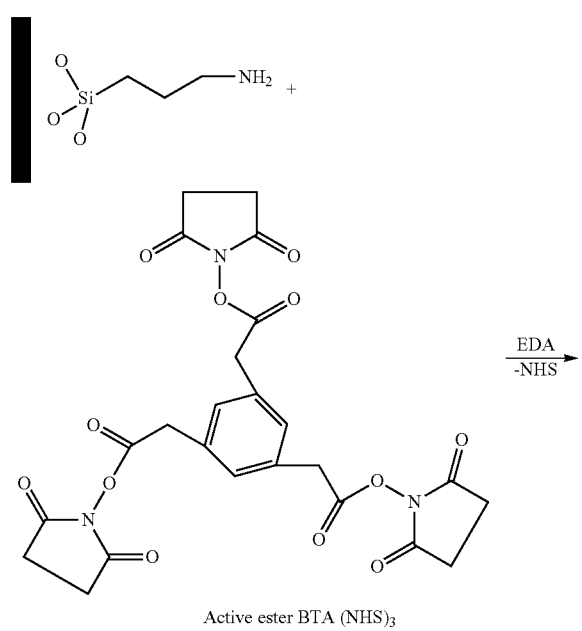

Active ester BTA (NHS)₃

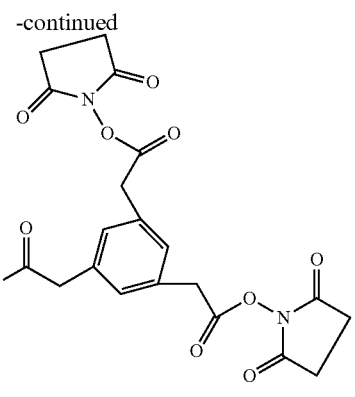

Protected BTA

Step 3: Conversion of Amine-Terminated Glass to Carboxylated Glass

The 8 channel glass chips were pre-treated and silanized with 5% aminopropyltriethoxysilane, as described in the materials and methods of WO 00/18957 (incorporated herein by reference).

Ester activation of BTA was carried out by reacting the following components:

| | | |
|---|---|---|
| 1,3,5-benzenetriacetic acid (BTA) | 60.5 mg | Fluka 17383 |
| N-Hydroxysuccinimide (NHS) | 99.5 mg | Fluka: 56480 |
| N,N'-Dicyclohexylcarbodiimide (DCC) | 149.6 mg | Fluka: 36650 |
| N-ethyldiisopropylamine (DIEA) | 41.2 µl | Perkin Elmer |
| DMF, anhydrous on molecular sieves SDS 0341021 | | |

The silanized glass channels were carboxylated by treatment with the activated BTA ester then washed with DMF, ethanol, water, 5% NaHCO₃ pH8.8 and water. The chips were dried under pure nitrogen and stored prior to use.

The BTA coated chips were grafted with the following oligonucleotide primers in a 1:1 ratio:

P5: NH₂-ss-AATGATACGGCGACCACCGA (SEQ ID NO: 1)

P7: NH₂-CAAGCAGAAGACGGCATACGA (SEQ ID NO: 2)

Grafting was carried out for 30 minutes at 50° C. in a grafting solution (70 µl per channel) containing 0.5 µM of each primer, 10 mM carbodiimide and 10 mM 1-methylimidazol.

After grafting of the P5 and P7 primers, an oligonucleotide denoted P5' (concentration of 500 nM) complementary to the grafted P5 oligonucleotide (5'-TCGGTGGTCGCCGTAT-CATT, no 5' terminal phosphate, SEQ ID NO:3) was hybridised to the grafted surface in channels 1 to 6 and 8, whilst channel 7 had no complementary P5' oligo hybridised. The hybridisation reaction was performed by heating the chip to 97.5° C., then cooling slowly to 40° C., then washing sequentially with 5×SSC, 0.3×SSC and 5×SSC.

The hybridisation of P5' to P5 on the surface creates a double stranded P5 adaptor on the surface. After the hybridization, the chip was washed for 5 minutes with milliQ water to remove salts.

First ligation reactions were set up on ice containing 5 µl 10× ligase buffer (NEB), 0.5 µl sonicated lambda DNA and 2.5 µl T4 DNA ligase (NEB) in a total volume of 50 µl per channel. Controls for this ligation reaction contained template and no ligase (channel 5), or ligase and no template (channel 6). Ligation reactions were pumped into the channels of the chip at room temperature, and left static for 1 hour. Channels were then washed with 0.1×SSC/0.1% Tween for 5 min and 5×SSC for 5 min. These first ligation reactions should ligate fragments of the sonicated lambda DNA onto the P5 adaptors on the surface of the chip.

Second ligation reactions were then set up on ice containing 5 µl 10× ligase buffer, 0.5 µl of a pre-annealed P7 adaptor and 2.5 µl T4 DNA ligase in a total volume of 50 µl per channel. The control for this ligation contained ligase and no adaptor (channel 4). These second ligation reactions were pumped into the channels of the chip at room temperature, and left static for 1 hour. Channels were then washed with 0.1×SSC/0.1% Tween for 5 min and 5×SSC for 5 min. These second ligation reactions should ligate the P7 adaptors onto the other ends of the lambda DNA fragments attached to the surface in the first ligation reactions.

```
P7 adaptor: 5'-CAAGCAGAAGACGGCATACGA (SEQ ID NO: 2)
            GTTCGTCTTCTGCCGTATGCT-5'
```

Both strands of the adaptor lacked 5' terminal phosphate groups. The adaptor sequence can be extended to include a sequencing primer in addition to the P7 sequence. Amplification using a P7 forward primer will result is copying the (universal) sequencing primer region as well as the (variable) target nucleic acid.

Klenow reactions were set up containing 5 µl of 10× ligase buffer, 0.165 µl of 10 mM dNTPs and 0.5 µl of Klenow polymerase (NEB) in a total volume of 50 µl per channel. The control for this reaction contained no Klenow enzyme (channel 3). These Klenow reactions were pumped into the channels of the chip at room temperature, and then the chip incubated at 25° C. for 15 min. Channels were then washed with 0.1×SSC/0.1% Tween for 5 min and 5×SSC for 5 min. The Klenow step aims to fill in the nicks present between the 3' OH of the ligated template strands and the 5' ends of the adaptors (non-phosphorylated).

Surface amplification using the grafted P5 and P7 primers and newly-created template strands was carried out by thermocycled amplification in an MJ Research thermocycler.

A typical amplification program is as follows:
1—97.5° C. for 0:45
2—57° C. for 1:30
3—73° C. for 1:30
4—Goto 1 [40] times
5—73° C. for 5:00
6—20° C. for 3:00
7—End As with any amplification reaction, the annealing temperature (step 2) depends on the primer pair that is used. Typical annealing temperatures are in the range of 55-58° C. For any given primer-pair the optimum annealing temperature can be determined by experiment. The optimum annealing temperature for P5/P7 primers was determined to be 57° C. The number of amplification cycles may be varied if required.

Amplification was carried out in a reaction solution comprising 1×PCR reaction buffer (supplied with the enzyme) 1M betain, 1.3% DMSO, 200 µM dNTPs and 0.025 U/µL Taq polymerase.

Figure 2A:
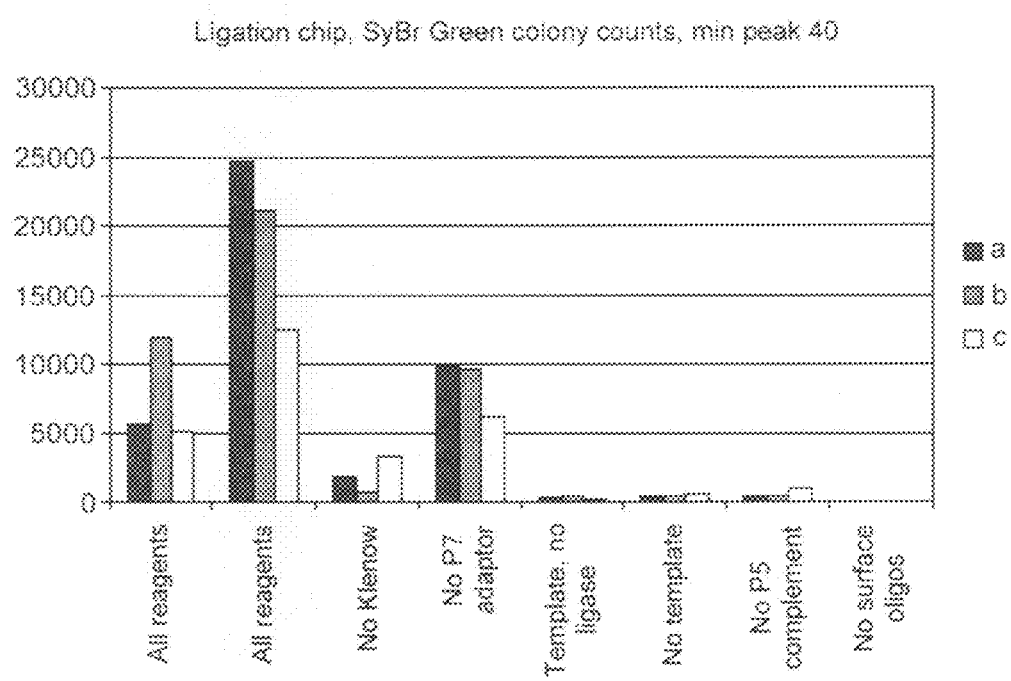
FIG. 2a graphically represents fluorescent imaging intensity (y axis) for an exemplary ligation reaction plus appropriate controls. (a), (b) and (c) represent the results of triplicate experiments.
Figure 2B:
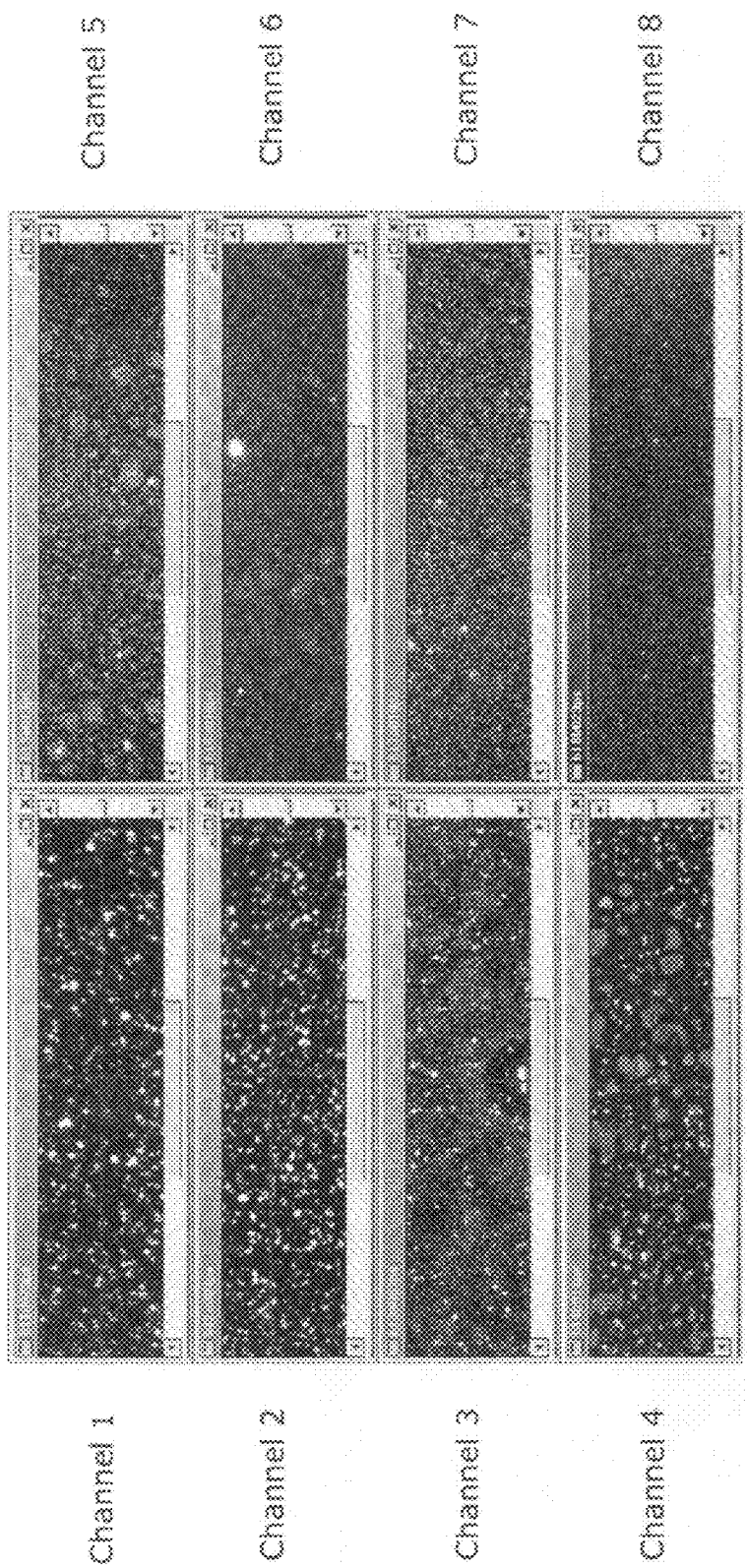
FIG. 2b shows actual fluorescence microscope images for an eight-channel chip treated as described in the accompanying experimental examples.

Following amplification the chips were stained with SyBr Green-I in TE buffer (1/10 000), using 100 µl per channel, and the amplified colonies visualised using objective 0.4, Filter Xf 22 and 1 second acquisition time (gain 1). The results are shown in FIG. 2.

TABLE 1 summary of reagents added to the chip

| Channel | Grafting oligos | Hyb oligo | 1$^{st}$ ligation | 2$^{nd}$ ligation | Klenow |
|---|---|---|---|---|---|
| 1 | P5/P7 | P5' | Target + ligase | Adaptor + ligase | + |
| 2 | P5/P7 | P5' | Target + ligase | Adaptor + ligase | + |
| 3 | P5/P7 | P5' | Target + ligase | Adaptor + ligase | − |
| 4 | P5/P7 | P5' | Target + ligase | Ligase only | + |
| 5 | P5/P7 | P5' | Target only | Adaptor + ligase | + |
| 6 | P5/P7 | P5' | Ligase only | Adaptor + ligase | + |
| 7 | P5/P7 | — | Target + ligase | Adaptor + ligase | + |
| 8 | — | P5' | Target + ligase | Adaptor + ligase | + |

Results

Clusters were clearly present in channels 1, 2 and 4, with a lower number of clusters in channel 3. The lack of clusters in channel 5 shows that ligase is required in the first ligation for successful template formation. The lack of clusters in channel 6 shows that the sonicated DNA target is also required in the first ligation for successful cluster formation—therefore the clusters formed in other channels of the chip are not the result of ligating adaptors together. Channel 7 shows that the complementary P5' oligo was needed to form the surface bound P5 adaptor, and channel 8 shows that the oligos grafted onto the surface are needed for cluster formation. The lower number of clusters in channel 3 indicates that the Klenow treatment is preferable but not critical for template formation—nick translation in this channel was probably partially completed by Taq polymerase during the first cycle of PCR.

The clusters were linearised using Tris(2-carboxyethyl)-phosphine hydrochloride (TCEP) to cleave the disulfide linkage as described in WO 06/064199.

Clusters can also be prepared on a polyacrylamide surface and linearised using sodium periodate as described in WO 06/064199.

The clusters can be heated to denature the cleaved strand, hybridised with a sequencing primer and sequenced according to the methods described in WO 06/064199.

The invention claimed is:

1. A method of preparing nucleic acid template constructs for solid-phase nucleic acid amplification which comprises performing the following ligation reactions a) and b):
   a) a ligation reaction in which the first end of one or more target polynucleotide molecules of unknown sequence are ligated to surface-bound adaptor polynucleotide molecules; and
   b) a ligation reaction in which solution-phase adaptor polynucleotide molecules are ligated to the second end of said target polynucleotide molecules of unknown sequence;
   thereby producing one or more template constructs attached to a solid support, wherein each of said template constructs comprises a target polynucleotide molecule of unknown sequence ligated to a surface-bound adaptor polynucleotide molecule and a solution-phase polynucleotide molecule, and wherein the target polynucleotide molecules are not digested with a cleavage reagent prior to step a).

2. A method according to claim 1 wherein ligation reaction a) is carried out before ligation reaction b).

3. A method according to claim 2 wherein the target polynucleotide molecules are fully or partially double stranded.

4. A method according to claim 3 wherein the surface-bound adaptor polynucleotide molecules are duplexes.

5. A method according to claim 4 which further comprises, prior to ligation reaction a), a step of annealing two single stranded polynucleotide molecules to form the surface-bound adaptor duplexes.

6. A method according to claim 5 wherein said annealing step is carried out in free solution to form adaptor duplexes which are attached to the solid support prior to ligation reaction a) to form surface-bound adaptor duplexes.

7. A method according to claim 5 wherein each surface-bound adaptor duplex is formed by annealing a complementary oligonucleotide to an amplification primer attached to the solid support.

8. A method according to claim 1 wherein the solution-phase adaptor polynucleotide molecules used in ligation reaction b) are duplexes.

9. A method according to claim 1 wherein the solid support has attached thereto a plurality of forward and/or reverse amplification primers.

10. A method according to claim 9 wherein the amplification primers attached to the solid support all contain identical template-specific nucleotide sequences.

11. A method according to claim 10 wherein the amplification primers attached to a solid support are all of identical structure and identical nucleotide sequence.

12. A method according to claim 9 wherein all the forward amplification primers attached to the solid support are of identical nucleotide sequence and structure and all the reverse amplification primers attached to the solid support are of identical nucleotide sequence and structure but the forward and reverse amplification primers are of different nucleotide sequence.

13. A method according to claim 1 wherein the target polynucleotides are all of identical nucleotide sequence.

14. A method according to claim 1 wherein the template constructs comprise a mixture of target polynucleotides of different nucleotide sequence.

15. A method according to claim 14 wherein the target polynucleotides are fragments of genomic DNA.

16. A method according to claim 15 wherein the target polynucleotides are fragments of human genomic DNA.

17. A method according to claim 14, wherein the mixture of target polynucleotides of different nucleotide sequence is a whole genome library of genomic DNA fragments.

18. A method according to claim 1 wherein the solution-phase adaptor and/or the surface-bound adaptor includes a sequence of nucleotides which permits annealing of a sequencing primer.

19. A method of amplifying nucleic acid template constructs by solid-phase nucleic acid amplification comprising:
   preparing template constructs for solid-phase amplification comprising one or more templates to be amplified using the method according to claim 1 and carrying out a solid-phase nucleic acid amplification reaction wherein said template constructs are amplified.

20. A method according to claim 19 wherein said template constructs are amplified by solid-phase amplification using forward and reverse amplification primers.

21. A method according to claim 20 wherein the forward and reverse amplification primers are all attached to the same solid support to which the target constructs are attached.

22. A method according to claim 20 wherein the reverse amplification primers are attached to the same solid support to which the template constructs are attached and the forward amplification primers are present in free solution in the amplification reaction.

23. A method of nucleic acid sequencing which comprises amplifying one or more nucleic acid template constructs using a method as defined in claim 19 and carrying out a sequencing reaction to determine the sequence of the whole or a part of at least one amplified nucleic acid strand produced in the amplification reaction.

24. The method of claim 23, wherein the sequencing reaction comprises sequencing-by-synthesis.

25. The method of claim 19, wherein the template constructs comprise a whole genome library of genomic DNA fragments.

26. The method of claim 1, wherein the target polynucleotide molecules are blunt ended.

27. The method of claim 20, wherein the adaptors comprise universal primer binding sites.

28. The method of claim 27, wherein the forward and reverse amplification primers bind to the universal primer binding sites.

29. The method of claim 28, wherein the forward and reverse amplification primers comprise different sequences.

30. The method of claim 28, wherein one of the amplification primers is attached to the solid support comprising the template constructs.

31. The method of claim 19, wherein the amplification reaction comprises amplifying the template constructs using a single primer.

32. The method of claim 1, further comprising fragmenting a nucleic acid molecule prior to step a) to produce the target polynucleotide molecules of step a).

* * * * *

UNITED STATES PATENT AND TRADEMARK OFFICE
CERTIFICATE OF CORRECTION

PATENT NO. : 8,168,388 B2  Page 1 of 1
APPLICATION NO. : 12/085508
DATED : May 1, 2012
INVENTOR(S) : Niall Anthony Gormley et al.

It is certified that error appears in the above-identified patent and that said Letters Patent is hereby corrected as shown below:

In Column 1, Line 4, Below the Title, insert

-- Cross Reference To Related Applications
The present application is a National Stage Application claiming the priority of copending PCT Application No. PCT/GB2006/004407, filed Nov. 24, 2006, which in turn, claims priority from Great Britain Application Serial No. GB 0524069.2, filed Nov. 25, 2005. Applicants claim the benefits of 35 U.S.C. § 120 as to the PCT application and priority under 35 U.S.C. § 119 as to the said Great Britain application, and the entire disclosures of both applications are incorporated herein by reference in their entireties. --.

Signed and Sealed this
Seventh Day of August, 2012

David J. Kappos
*Director of the United States Patent and Trademark Office*